United States Patent [19]

Mich et al.

[11] 4,315,014

[45] Feb. 9, 1982

[54] ANTIBACTERIAL AMIDE COMPOUNDS AND PHARMACEUTICAL COMPOSITION CONTAINING THE SAME

[75] Inventors: Thomas F. Mich, Ann Arbor, Mich.; Leonard Doub, Tucson, Ariz.

[73] Assignee: Warner-Lambert Company, Morris Plains, N.J.

[21] Appl. No.: 190,109

[22] Filed: Sep. 24, 1980

[51] Int. Cl.³ .................. A61K 31/44; C07D 499/70; C07D 211/76; C07D 213/64

[52] U.S. Cl. ............................. 424/263; 260/239.1; 424/266; 546/261; 546/288; 546/293

[58] Field of Search ................... 260/239.1; 424/263, 424/266; 546/288, 261, 293

[56] References Cited

U.S. PATENT DOCUMENTS

| | | | |
|---|---|---|---|
| 3,873,523 | 3/1975 | Doub et al. | 260/239.1 |
| 3,951,955 | 4/1976 | Tobiki et al. | 260/239.1 |
| 4,031,230 | 6/1977 | Gottschlich et al. | 424/263 |
| 4,092,309 | 5/1978 | Mich | 260/239.1 |
| 4,101,661 | 7/1978 | Kaltenbronn et al. | 424/266 |

Primary Examiner—Natalie Trousof
Assistant Examiner—Vera C. Clarke
Attorney, Agent, or Firm—Stephen Raines

[57] ABSTRACT

Novel organic amide compounds which are N-[6-(sulfonylaminophenyl)-1,2-dihydro-2-oxonicotinoyl]-penicillin compounds having broad spectrum antibacterial utility are provided by (a) reacting the free amino acid of the appropriate penicillin or the acid salt or silylated derivative or complex thereof with a reactive derivative of the corresponding N-6-(sulfonylaminophenyl)-1,2-dihydro-2-oxonicotinic acid or (b) reacting the free amino acid 6-aminopenicillanic acid or a related compound or the acid salt or silylated derivative thereof with a reactive derivative of the corresponding D-N-[6-(sulfonylaminophenyl)-1,2-dihydro-2-oxonicotinoyl]-2-substituted glycine. Pharmaceutical compositions containing said compounds and methods for treating infections using said compositions are also disclosed.

14 Claims, No Drawings

ANTIBACTERIAL AMIDE COMPOUNDS AND PHARMACEUTICAL COMPOSITION CONTAINING THE SAME

SUMMARY AND DETAILED DESCRIPTION

The present invention relates to novel chemical compounds that are useful as pharmacological agents and to methods for their production. More particularly, the invention relates to novel organic amide compounds having the formula

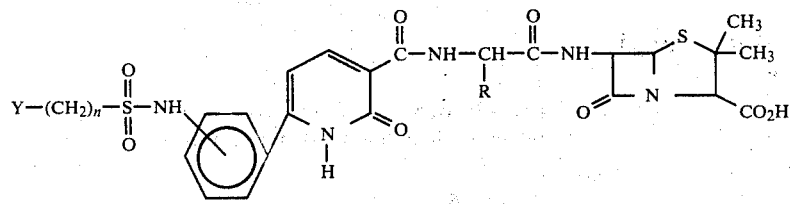

and pharmaceutically acceptable salts thereof; wherein Y is hydrogen, $CF_3$, hydroxy, pyridyl,

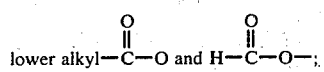

n is 0, 1, 2, or 3 and R is phenyl, 4-hydroxyphenyl, 2-thienyl or cyclohexa-1,4-dien-1-yl with the proviso that when Y is

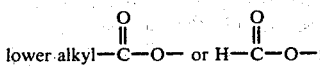

n is 1, 2, or 3.

Lower alkyl is defined as a hydrocarbon fragment of from one to six carbon atoms.

In accordance with the invention the foregoing amide compounds having the formula

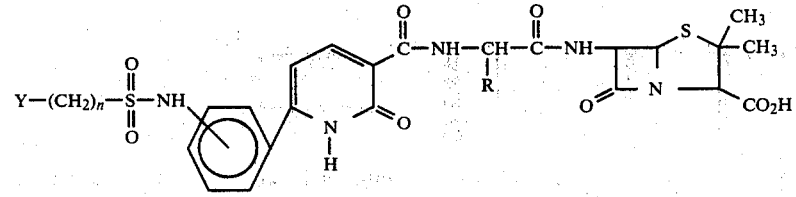

and pharmaceutically acceptable salts thereof wherein Y, n and R are as previously defined are produced by reacting a compound of the formula

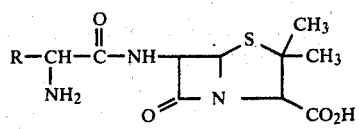

or the basic salt, silylated derivative (preferably the disilylated) or complex (preferably the dimethylsulfoxide) thereof wherein R is as previously defined, with a reactive derivative of a 1,2-dihydro-2-oxonicotinic acid compound having the formula

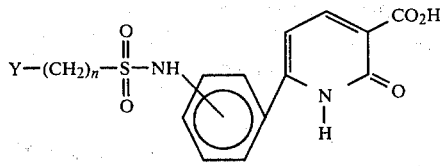

or its acid addition salt, where Y and n all have the aforementioned significance.

Some examples of reactive derivatives of the 6-(substituted)-1,2-dihydro-2-oxonicotinic acid compound suitable for the reaction are the acid halides (especially the acid chloride), the imidazolide, mixed anhydrides (especially those formed from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (oxonicotinic acid compound or amino acid compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin compounds in the free acid or salt form, aqueous solutions may be used for acylation with an acid halide or mixed anhydride under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of 6-(substituted)-1,2-dihydro-2-oxonicotinic acid compounds, which are required as starting materials in the foregoing process, can be prepared according to any of a variety of methods.

A 6-(substituted)-1,2-dihydro-2-oxonicotinic acid may be converted to its acid chloride utilizing thionyl chloride, its mixed anhydride utilizing ethyl chloroformate, its pentachlorphenyl ester by esterification with pentachlorophenol and its imidazolide by reacting the acid with 1,1′-carbonyl-diimidazole.

Compounds of the formula

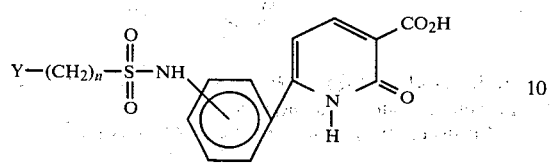

where Y and n are as previously defined are prepared by acylation of a compound of the formula

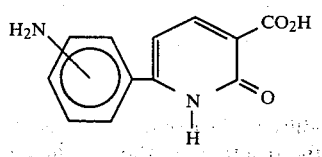

with a compound of the formula

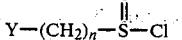

wherein Y and n are as previously defined preferably with the aid of trimethylsilylchloride.

The compound of the formula

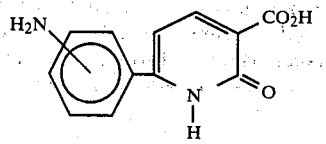

is prepared by hydrolyzing a compound of the formula

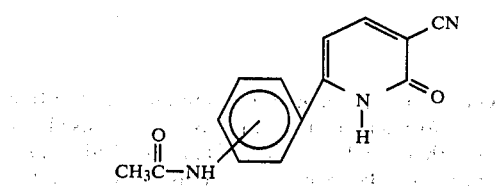

which is in turn prepared by coupling a compound of the formula

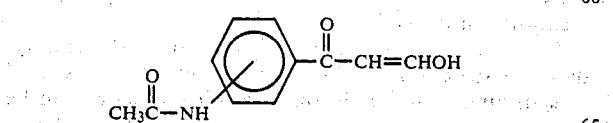

with 2-cyanoacetamide.

The compound of the formula

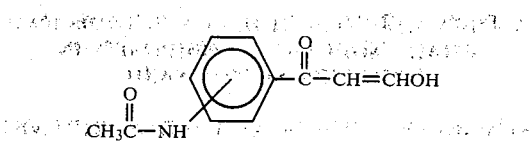

is prepared by formylating a compound of the formula

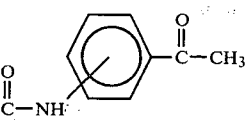

The silylated amino acid starting materials can be prepared by reacting an amino acid of the formula

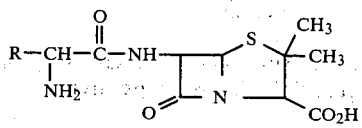

or a salt thereof wherein R is as previously defined in anhydrous form with either one or two equivalents of a tri(lower alkyl)silyl chloride in the presence of triethylamine. The preferred silylating agents are trimethylsilyl chloride and dimethyl dichlorosilane. When two equivalents of the silylating agent are used, both the amino and the carboxyl group become silyated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

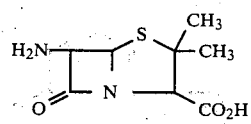

or the corresponding acid salt or silylated derivative thereof with a reactive derivative of D-N-[6-(substituted)-1,2-dihydro-2-oxonicotinoyl]-2-substituted glycine having the formula

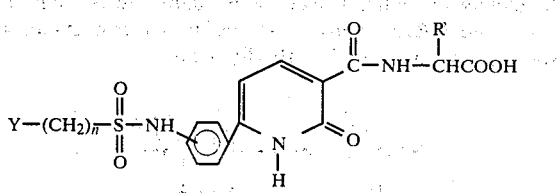

or its acid addition salts where Y, n and R have the aforementioned significance.

Some examples of reactive derivatives of the D-N-(1,2-dihydro-2-oxonicotinoyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (oxonicotinic acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 6-aminopenicillanic acid may be reacted with an acid chloride or mixed anhydride in the free acid or salt form using aqueous solutions under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of D-N-[6-(substituted)-1,2-dihydro-2-oxonicotinoyl]-2-substituted glycines or their acid-addition salts which are required as starting materials in the foregoing process can be prepared by methods illustrated in greater detail hereinafter.

D-N-[6-substituted)-1,2-dihydro-2-oxonicotinoyl]-2-substituted glycine compounds may be prepared by reacting the corresponding reactive derivative of 6-(substituted)-1,2-dihydro-2-oxonicotinic acid, such as the acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

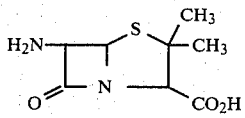

with a standard silylating agent such as chlorotrialkylsilane, hexaalkyldisilazane, etc. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically-acceptable salts are formed by reacting the free acids with such bases as sodium hydroxide, sodium carbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salts forms are the alkali metal salts. The carboxylate salts are converted to the free acids by acidification. The free acids and their carboxylate salts usually differ somewhat in solubility properties but, in general, are otherwise equivalent for the purposes of the invention.

The compounds of the invention can exist in anhydrous form, as well as in solvated, including hydrated, forms. In general, the hydrated forms and the solvated forms with pharmaceutically acceptable solvents are equivalent to the anhydrous or unsolvated forms for the purposes of the invention.

The pyridone segment of the compounds of this invention may be capable of undergoing keto-enol tautomerism to give 2-hydroxypyridines. Such a tautomer is equivalent to the pyridones for the purposes of the inventions and are included within the above shown structures.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their non-toxic pharmaceutically acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg at about 1000 mg of active compound per unit dose form.

The invention is illustrated by the following examples.

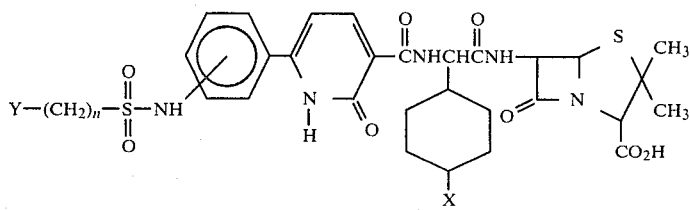

ACTIVITY TABLE
Minimal Inhibitory Concentration (μg/ml)

| Y—(CH$_2$)$_n$— | X | NH | Pseudomonas aeruginosa #28 | Entero. cloacae | Serr. marces. | Klebs. pneu. | Staph. aureus S18713 |
|---|---|---|---|---|---|---|---|
| CH$_3$ | H | 3 | 12.5 | 6.3 | 25 | 1.6 | >200 |
| CH$_3$ | H | 4 | 3.1 | 6.3 | 50 | 3.1 | 100 |
| CH$_3$ | OH | 4 | 1.6 | 3.1 | 100 | 3.1 | 100 |
| C$_3$H$_7$ | H | 4 | 3.1 | 6.3 | 50 | 3.1 | 100 |
| CF$_3$ | H | 4 | 6.3 | 6.3 | 200 | 3.1 | 200 |
| CF$_3$ | OH | 4 | 12.5 | 6.3 | 50 | 25 | 25 |
| AcO(CH$_2$)$_3$ | H | 4 | 6.3 | 6.3 | 100 | 3.1 | 100 |
| N◯◯—CH$_2$CH$_2$ | H | 4 | 6.3 | 6.3 | 100 | 3.1 | 100 |
| N—◯◯ | H | 3 | 12.5 | 12.5 | 100 | 6.3 | >200 |
| N—◯◯ | H | 4 | 12.5 | 12.5 | 100 | 6.3 | 100 |

STARTING MATERIALS

6-(4-Aminophenyl)-1,2-dihydro-2-oxonicotinic acid

A suspension of 330 g (6.1 mol) of sodium methoxide, 3 L of tetrahydrofuran, and 2.5 L of ether is stirred at room temperature and a suspension of 490 g (2.77 mol) of 4-(acetylamino)acetophenone, 416 g (5.54 mol) ethyl formate, and 3 L of tetrahydrofuran is added over a period of 1 hour. The suspension is stirred at room temperature overnight under nitrogen. The precipitate is allowed to settle and the solvent drawn off with a filter candle. Another 3 L of tetrahydrofuran is added and the solvent again removed by filter candle.

Water (9 L) is added to the residue and the pH is adjusted to 9.0 with glacial acetic acid and 388 g (4.6 mol) of 2-cyanoacetamide is added. The mixture is warmed to 90° on a steam bath while allowing the residual tetrahydrofuran and ether to escape. The system is fitted with a condenser and heated at this temperature overnight. The suspension is cooled and the pH is adjusted to 5.8 with acetic acid. The brown solid is filtered and washed with water, 1:1 methanol water, methanol and finally ethyl acetate. Drying affords 422 g of 6-(4-acetylaminophenyl)-1,2-dihydro-2-oxonicotinonitrile; mp>350°.

A suspension of 422 g (1.67 mol) of the above nitrile and 3650 mol of water containing 932 g of potassium hydroxide is heated at 105° for 40 hrs. The solution is cooled and acidified to pH 4.0 with 1360 ml of concentrated hydrochloric acid and 400 g of potassium hydroxide pellets are added with stirring. After filtration, the pH of the filtrate is adjusted to 4.5 with concentrated hydrochloric acid. The solid is filtered, suspended in 8 L of water and filtered. The solid is washed with methanol and finally ethyl acetate and dried at 60° to give 328 g of the title compound; mp>314°–316° dec. $E_1^1 = 944$ λ347 nm pH 7

6-(3-Aminophenyl)-1,2-dihydro-2-oxonicotinic acid

A stirred suspension of 71.3 g (1.32 mol) of sodium methoxide, 500 ml of tetrahydrofuran and 300 ml of ether is cooled to 0°–5° under nitrogen and a solution of 106.3 g (0.6 mol) of 3-(acetylamino)acetophenone, 96.04 (1.2 mol) of ethyl formate, 700 ml of dry acetonitrile, and 350 ml of tetrahydrofuran is added during 30 minutes. The reaction is allowed to warm to room temperature with stirring overnight. The organic solvents are decanted from the solids and the solids dissolved in 2.25 L of water. The pH is adjusted to 9.0 with glacial acetic acid and 84.1 g (1.0 mol) of 2-cyanoacetamide is added. The solution is heated at reflux for 3.5 hours, cooled and filtered. The solids are washed with water, acetonitrile, and ether and dried to give 93.1 g of 6-(3-acetylaminophenyl)-1,2-dihydro-2-oxonicotinonitrile; mp 326°–328°.

$$E_1^1 = \left. \begin{array}{cc} 768 & \lambda\ 350nm \\ 890 & 242 \end{array} \right\} \text{pH 7}$$

A mixture of 92.6 g (0.37 mol) of the above nitrile, 185 g of potassium hydroxide, and 740 ml of water is heated at 105° for 30 hrs. The cooled reaction mixture is poured into 285 ml of concentrated hydrochloric acid and ice. The pH of the suspension is adjusted to 5.0 with aqueous sodium hydroxide solution and the solid filtered, washed with water, and dried to give 81.2 g of the title compound.

$$E_1^1 = \begin{matrix} 650 & \lambda & 329\text{nm} \\ 825 & & 227 \end{matrix} \Bigg) \text{pH 7}$$

EXAMPLE 1

N-[6-[3-(Methylsulfonylamino)phenyl]-1,2-dihydro-2-oxonicotinoyl]ampicillin

A suspension of 1.15 g (5 mmol) of 6-(3-aminophenyl)-1,2-dihydro-2-oxonicotinic acid, 200 ml of water, and 0.42 g (5 mmol) of sodium bicarbonate is stirred at 0°–5° and a solution of 3.6 ml (30 mmol) of methanesulfonyl chloride and 30 ml of acetonitrile is added over a 2 hr. period. During the addition, the pH of the reaction is maintained at 6.9–7.3 with 1 N sodium hydroxide. After the addition, the reaction is stirred at 0°–5° for 2 hrs. The precipitated solid is filtered and dried to give 0.45 g of 6-[3-(methylsulfonylamino)phenyl]-1,2-dihydro-2-oxonicotinic acid.

A suspension of 0.925 g (3 mmol) of the above acid and 50 ml of thionyl chloride is stirred at 50° for 2 hrs. and at 25° for 16 hrs. The reaction is diluted with 300 ml of hexane and the precipitated solid is filtered, washed with hexane and dried to give 0.98 g of 6-[3-(methylsulfonylamino)phenyl]-1,2-dihydro-2-oxonicotinic acid chloride.

A suspension of 1.35 g (3 mmol) of ampicillin triethylamine salt and 150 ml of tetrahydrofuran is stirred at 0°–5° and 1.2 ml (9 mmol) of chlorotrimethylsilane is added followed by 1.7 ml (12 mmol) of triethylamine. The ice bath is removed and the mixture is stirred at 25° for 20 minutes. The reaction is cooled to 0°–5° and 0.98 g (3 mmol) of the above acid chloride is added. The mixture is stirred at 0°–5° for 30 minutes and at room temperature for 4 hours. The solid is filtered off and the filtrate is evaporated under reduced pressure. The residue is treated with 100 ml of water and the pH is adjusted to 7.8 and the insoluble material is filtered off. The pH of the filtrate is adjusted to 3.0 and the suspension is extracted with 50 ml ethylacetate twice. The combined organic layer is dried and 1.0 ml (3 mmol) of 50% sodium 2-ethylhexanoate in butanol is added. The solid is filtered, washed with ether, and dried to give the title penicillin as the sodium salt; $[\alpha]_D^{23} + 170°$ (c1, 75% DMF/pyridine).

$E_1^1$ 290 λ349 nm 2.5% DMF/pyridine

EXAMPLE 2

N-[6-[4-(Methylsulfonylamino)phenyl]-1,2-dihydro-2-oxonicotinoyl]ampicillin

A suspension of 23.02 g (0.1 mol) of 6-(4-aminophenyl)-1,2-dihydro-2-oxonicotinic acid, 1 L of dichloromethane, and 42.0 ml (0.303 mol) of triethylamine is stirred at 0°–5° and 42.17 ml (0.33 mol) of chlorotrimethylsilane is added. The ice bath is removed and the mixture is stirred at room temperature for 1 hr. The hazy solution is cooled to 10° and 23.8 ml (0.31 mol) of methanesulfonyl chloride is added. The resulting solution is stirred at room temperature for 24 hours and the dichloromethane is evaporated under reduced pressure and 500 ml of water is added to the residue. The mixture is cooled to 10° and the solid is filtered, washed with water, acetonitrile, and ether, and dried to give 29.9 of 6-[4-(methylsulfonylamino)phenyl]-1,2-dihydro-2-oxonicotinic acid; mp>320°.

A solution of 92.5 g (30 mmol) of the above acid, 7.3 g (45 mmol) of 1,1-carbonyldiimidazole, and 92 ml of N,N-dimethylacetamide is stirred at +60° C. for 30 min and at room temperature overnight. The reaction suspension is first cooled in an ice bath, then the solid is filtered off, washed with N,N-dimethylacetamide, ether, and dried to give 6.08 g of 6-[4(methylsulfonylamino)phenyl[-1,2-dihydro-2-oxonicotinic acid imidazolide.

A mixture of 10.8 g (24 mmol) of ampicillin triethylamine salt and 100 ml of dry N,N-dimethylacetamide is stirred at 0°–5° and 6.74 ml (52.8 mmol) of chlorotrimethylsilane is added followed by 4.03 ml (28.8 mmol) of triethylamine. The ice bath is removed and the mixture is stirred at room temperature for 30 min. The reaction is cooled to 0°–5° and 5.5 g (15.4 mmol) of the above imidazolide is added. The resulting mixture is stirred at room temperature for 2.5 hr and is allowed to stand at 0° overnight. The reaction is filtered and the filtrate is poured into 800 ml of cold water. The pH is adjusted to 2.5 with 6.6 N hydrochloric acid. The precipitated solid is filtered and washed with water and dissolved in 45 ml of tetrahydrofuran and 300 ml of ethyl acetate. The organic phase is extracted with 100 ml of water and the aqueous phase is washed twice with a solution of 7 ml of tetrahydrofuran and 50 ml of ethyl acetate. The combined organic layers are dried over magnesium sulfate treated with charcoal and filtered. A 5.31 ml portion of 50% sodium 2-ethylhexanoate in n-butanol is added to the filtrate and the precipitate is filtered, washed with ethyl acetate and ether, and dried under high vacuum over phosphorus pentoxide at room temperature for 2 days to give 7.6 g of the title penicillin as the sodium salt; $[\alpha]_D^{23} + 326°$ (c1, pH7).

$$E_1^1 \begin{matrix} 415 & \lambda & 355\text{nm} \\ 152 & & 251 \end{matrix} \text{ pH 7}$$

EXAMPLE 3

N-[6-[4-(methylsulfonylamino)phenyl[-1,2-dihydro-2-oxonicotinoyl]amoxicillin

A stirred suspension of 4.43 g (10.6 mmol) of amoxicillin trihydrate, and 124 ml of N,N-dimethylacetamide is stirred at 0°–5° and 8.45 ml (64.6 mmol) of chlorotrimethylsilane is added followed by 9.94 ml (70.8 mmol) of triethylamine. The ice bath is removed for 30 min and then replaced again. Three grams (8.7 mmol) of the imidazolide from Example 2 is added at 0°–5° C. The ice bath is removed and stirring at room temperature is continued for three hours, and the reaction mixture is stored at 0° C. overnight. Insoluble material is filtered off and the filtrate is poured into 1.0 liter of ice water. The pH is adjusted to 2.2 with 1 N hydrochloric acid and the precipitated solid is filtered, resuspended in cold water, pH adjusted with 1 N sodium hydroxide to 7.8, filtered and the filtrate lyophilized to give 3.3 g of the title penicillin as the sodium salt; $[\alpha]_D^{23} + 189°$ (c1, 75% DMF/pyridine).

$E_1^1$ 376λ356 nm pH 7

EXAMPLE 4

N-[6-[4-(Propylsulfonylamino)phenyl]-1,2-dihydro-2-oxonictinoyl]ampicillin

A suspension of 10.4 g (45 mmol) of 6-(4-aminophenyl)-1,2-dihydro-2-oxonicotinic acid, 18.9 ml (135 mmol) of triethylamine, and 475 ml of dichloromethane is stirred at 0°–5° and 19.5 ml (148.5 mmol) of chlorotrimethylsilane is added. The ice bath is removed and the reaction mixture stirred at room temperature for 1 hr. the reaction is cooled to 0°–5° and 19.3 g (135 mmol) of 1-propanesulfonyl chloride is added. The ice bath is removed after 15 min and the reaction is stirred at room temperature for 24 hrs and 18.9 (135 mmol) of triethylamine is added and stirring is continued at room temperature overnight. The mixture is treated with 8.1 ml (0.45 mol) of water and the dichloromethane is evaporated. Water is added to the residue and the solid is filtered, washed with water and ether, and dried. The product is suspended in 200 ml of water and the pH is adjusted to 8 with solid sodium bicarbonate and the mixture is heated on the steam bath overnight. The solution is clarified by filtration and the filtration is acidified with 1 N hydrochloric acid and the precipitated solid is filtered, washed with water and ether, and dried to give 13.6 g of yellow solid. This material is pulverized and heated at reflux with stirring for 1 hr with 400 ml of methanol. The solid is filtered, washed with methanol and ether, and dried to give 10.7 g of 6-[4-(propylsulfonylamino)phenyl]-1,2-dihydro-2-oxonicotinic acid; mp>260°.

A mixture of 6.7 g (20 mmol) of the above pyridone acid 4.5 g (28 mmol) of carbonyldiimidazole, and 80 ml of N,N-dimethylacetamide is stirred at 60°–65° for 30 min and at room temperature for 1 hr. The solution is cooled with an ice bath and about 900 ml of ether is added. The solid is filtered, washed with ether, and dried to give 6.6 g of 6-[4-(propylsulfonylamino)-phenyl]-1,2-dihydro-2-oxonicotinic acid imidazolide.

A suspension of 9.0 g (20 mmol) of ampicillin triethylamine salt and 160 ml of N,N-dimethylacetamide is stirred at 0°–5° and 5.1 ml (40 mmol) of chlorotrimethylsilane is added followed by 2.8 ml (20 mmol) of triethylamine. The ice bath is removed and the reaction mixture is stirred at room temperature for 45 min Ice bath cooling is resumed and 6.6 g (17 mmol) of the above imidazolide is added. Stirring is continued at 0°–5° for 15 min and at room temperature for 3.75 hrs. The reaction mixture is poured into 1200 ml of ice water and the pH is adjusted to 2.5 with 1 N hydrochloric acid. The precipitated solid is filtered, washed with water and ether, and dried under high vacuum overnight. The crude solid is dissolved in 112 ml of N,N-dimethylacetamide and 7.3 ml (22 mmol) of sodium 2-ethyl-hexanoate (50% in n-butanol) is added. The solution is diluted with 300 ml of ethyl acetate and the gummy precipitate is filtered and discarded. The filtrate is further diluted with 300 ml of ethyl acetate and the precipitated solid is filtered, dissolved in 150 ml of water and lyophilized. The lyophilized solid is redissolved in 120 ml of water and reliophilized to give 6.19 g of the title penicillin as the sodium salt; $[\alpha]_D^{23} +167°$ (cl, 75% DMF/pyridine).

$$E_1^1 \, {}^{372}_{131} \, \lambda \, {}^{359nm}_{363} \quad pH \, 7$$

EXAMPLE 5

N-[6-[4-(Trifluoromethylsulfonylamino)phenyl]-1,2-dihydro-2-oxonicotinoyl]ampicillin A suspension of 1.38 g (6 mmol) of 6-(4-aminophenyl)-1,2-dihydro-2-oxonicotinic acid, 60 ml of dichloromethane, and 2.6 ml (18 mmol) of triethylamine is stirred at 0°–5° and 2.6 ml (19.8 mmol) of chlorotrimethylsilane is added. The ice bath is removed and the mixture is stirred at room temperature for 1 hr. The solution is cooled to −78° and 2.26 ml (12 mmol) of trifluoromethanesulfonic anhydride is added. The reaction is stirred at −78° to 25° for 1½ hours and at 25° for 3 hrs. The dichloromethane is evaporated under reduced pressure and the resulting solid is treated with water and filtered. The filter cake is washed with water and ether and dried to give 2.06 g of 6-[4-(trifluoromethylsulfonylamino)phenyl]-1,2-dihydro-2-oxonicotinic acid; mp>260° C.

A suspension of 4.2 g (11.8 mmol) of the above acid, 2.4 g (14.8 mmol) of carbonyldiimidazole, and 50 ml of tetrahydrofuran is stirred at 25° for 1¼ hrs and at 65° for 15 min. The mixture is cooled and filtered. The solid is washed with ether and dried to give 4.7 g of 6-[4-(trifluoromethylsulfonylamino)phenyl]-1,2-dihydro-2-oxonicotinic acid imidazolide.

A suspension of 4.95 g (11 mmol) of ampicillin triethylamine salt and 80 ml of N,N-dimethylacetamide is stirred at 0°–5° and 2.82 ml (22 mmol) of chlorotrimethylsilane is added, followed by 1.54 ml (11 mmol) of triethylamine. The ice bath is removed and the mixture is stirred at 25° for 20 min. The reaction mixture is cooled to 0°–5° and 4.12 g (10 mmol) of the above imidazolide is added. The reaction is stirred at 0°–5° for 30 min and at 25° for 3 hrs and poured into 600 ml of ether. The liquid is decanted and the gummy residue is dissolved in 500 ml of ice water. The pH is adjusted to 7.0 and filtered. The filtrate is acidified to pH 2.5 with 1 N hydrochloric acid. The precipitated solid is filtered and washed with water and dried under vacuum. The dried solid is dissolved in 100 ml of tetrahydrofuran and 1.7 ml (15 mmol) of 50% sodium 2-ethylhexanoate in butanol is added. The solid is filtered and washed with ether and dried under vacuum to give 2.37 g of the title penicillin as sodium salt; $[\alpha]^{23} +109°$ (cl, pH 7).

$E_1^1 \, 365\lambda362$ nm pH 7

EXAMPLE 6

N[6-[4-(Trifluoromethylsulfonylamino)phenyl]-1,2-dihydro-2-oxonicotinoyl]amoxicillin A suspension of 3.35 g (5.5 mmol) of amoxicillin dimethyl sulfoxide complex and 60 ml of N,N-dimethylacetamide is stirred at −5° C. and 2.06 g (5 mmol) of the imidazolide from Example 5 is added. The reaction is stirred at 0°–5° for 1 hr and at room temperature for 2 hrs. The reaction mixture is poured into 500 ml of ice water and the pH is adjusted to 2.5 with 1 N hydrochloric acid. The precipitated solid is filtered and washed with water and dried under vacuum. The dried solid is dissolved in 20 ml on N,N-dimethylacetamide and 6.5 ml (8.0 mmol) of 0.81 M sodium 2-ethylbutyrate in tetrahydrofuran is added followed by 500 ml of ethyl acetate. The solid is filtered and washed with ether and dried to give 2.6 g of title penicillin as sodium salt; $[\alpha]_D^{23} +146°$ (cl, 75% DMF/pyridine).

$E_1^1 \, 324\lambda362$ nm pH 7

EXAMPLE 7

N-[6-[4-[3-(acetyloxy)propylsulfonylamino]phenyl]-1,2-dihydro-2-oxonicotinoyl]ampicillin A mixture of 81 g (0.5 mol) of 3-hydroxy-1-propanesulfonic acid sodium salt and 250 ml of acetic anhydride is heated on the steam bath for 64 hrs and at reflux for 2 hrs. The dark solution is cooled and the solid is filtered, washed with ether and dried to give 82.8 g of 3-acetyloxy-1-propanesulfonic acid sodium salt.

A 100 g (0.48 mol) portion of phosphorus pentachloride is added to a flask containing 82.0 g (0.4 mol) of the above sulfonic acid salt. When the initial reaction subsides, the mixture is heated on the steam bath for 1 hr and 25 g of phosphorus pentachloride is added. Heating is continued for another 2.5 hr and another 10 g of phosphorus pentachloride is added and heating continued for 30 min. The dark reaction mixture is cooled and filtered and the filtrate distilled. The clear distillate is redistilled to give 42.3 g of 3-acetyloxy-1-propanesulfonyl chloride; bp 69°–81°/0.03 mm.

A suspension of 6.9 g (30 mmol) of 6-(4-aminophenyl)-1,2-dihydro-2-oxonicotinic acid, 12.6 ml (90 mmol) of triethylamine, and 300 ml of dichloromethane is stirred at 0°–5° and 12.1 ml (94.5 mmol) of chlorotrimethylsilane is added. The ice bath is removed and the reaction mixture is stirred at room temperature for 1.5 hrs. The solution is cooled with an ice bath and 12.04 g (60 mmol) of 3-acetoxy-1-propanesulfonyl chloride is added and the solution is stirred overnight at room temperature. An additional 6.0 g (30 mmol) of 3-acetoxy-1-propanesulfonyl chloride is added and stirring is continued overnight at room temperature. The dichloromethane is evaporated and water is added to the residue. The resulting solid is filtered, washed with water and ether, and air dried to give 11.8 g of yellow solid. The material is heated at reflux for 1 hr with stirring in 160 ml of methanol and ether and dried. The process is repeated to give 6.9 g of a yellow powder which is combined with 1.3 g from another run for further purification. The 8.2 g of solid is heated on a steam bath in 120 ml of acetic acid and 3 ml of acetic anhydride overnight and filtered. Crystals are formed in the cooled filtrate and filtered and dried to give 3.0 g. The insolubles are heated to boiling in 100 ml of acetic acid and 4 ml of acetic anhydride on a hot plate and filtered hot. On cooling crystals are formed in the filtrate and are isolated as before to give 3.4 g. The two crops are combined (6.4 g) and stirred with 128 ml of methanol for 30 min at room temperature and filtered. The solid is washed with ether and dried to give 5.8 g of yellow powder. This material is heated on a steam bath with 17 ml of N,N-dimethylacetamide for 20 min, cooled, and filtered. The filtrate is added to 130 ml of methanol and crystals formed. The crystalline solid is filtered, washed with methanol and ether, and dried to give 5.4 g of 6-[4-[3-(acetyloxy)propylsulfonylamino]phenyl]-1,2-dihydro-2-oxonicotinic acid.

A suspension of 5.2 g (13.2 mmol) of the above acid, 3.18 g (19.5 mmol) of carbonyldiimidazole and 100 ml of tetrahydrofuran is refluxed for 15 min and then cooled to 0°–5°. The solid is filtered off, washed with 10 ml of tetrahydrofuran and ethyl ether. The dried 6-[4-[3(acetyloxy)propylsulfonylamino]phenyl]-1,2-dihydro-2-oxonicotinic acid imidazolide weighs 5.12 g.

A suspension of 5.06 g (11.25 mmol) ampicillin triethylamine salt and 30 ml of N,N-dimethylacetamide is stirred at 0°–5° and 3.15 ml (24.2 mmol) of chlorotrimethylsilane is added followed by 1.89 ml (13.5 mmol) of triethylamine. The ice bath is removed and the mixture is stirred at room temperature for 20 min. The reaction mixture is cooled to 0°–5° and 3.21 g (7.5 mmol) of the above imidazolide is added. The ice bath is removed and stirring at room temperature is continued for three hours. Insoluble material is filtered off and the filtrate is poured into 500 ml of ice water. The pH is adjusted to 2.5 with 1H hydrochloric acid and the precipitated solid is filtered, washed with water and suspended in 100 ml of cold water. The pH adjusted to 7.0 with 1 N sodium hydroxide and the solution is clarified by filtration and lyophilized to give 4.78 g of the title penicillin as the sodium salt; $[\alpha]_D^{23} +161°$ (cl, 75% DMF/pyridine).

$E_1^1 348$ $\lambda 358$ nm pH 7

EXAMPLE 8

N-[6-4-[2-(4-pyridinyl)ethylsulfonylamino]phenyl]-1,2-dihydro-2-oxonicotinoyl]ampicillin A suspension of 121.7 g (0.65 mmol) of 4-pyridineethanesulfonic acid and 488 ml of phosphorus oxychloride is stirred at room temperature under nitrogen and 148.9 g (0.72 mol) of phosphorus pentachloride is added. The mixture is stirred at 60° for 1.5 hr and cooled and 488 ml of carbon tetrachloride is added. The solid is filtered, washed with carbon tetrachloride, acetonitrile and ether and dried under high vacuum over solid sodium hydroxide to give 142.9 g of 4-pyridineethanesulfonyl chloride hydrochloride.

A suspension of 11.5 g (50 mmol) of 6-(4-aminophenyl)-1,2-dihydro-2-oxonicotinic acid, 21 ml (150 mmol) of triethylamine and 500 ml of dichloromethane is stirred at 0°–5° and 20.2 ml (158 mmol) of chlorotrimethylsilane is added. The ice bath is removed and the mixture is stirred at room temperature for 1 hr. The solution is cooled with an ice bath and 13.4 (55 mmol) of 4-pyridineethanesulfonyl chloride hydrochloride is added followed by 7 ml (50 mmol) of triethylamine 15 min later. The reaction is stirred at room temperature for 70 hrs, cooled with an ice bath, and 3.5 ml (25 mmol) of triethylamine is added. The mixture is stirred at room temperature for 4.5 hrs, cooled with an ice bath and 7.6 g (27.5 mmol) of 4-pyridineethanesulfonyl chloride hydrochloride is added. The mixture is stirred at room temperature for 16 hrs, cooled with an ice bath and 3.5 ml (25 mmol) of triethylamine is added and stirring continued for 4.5 hrs at room temperature. Cooling is resumed and 7.6 g (27.5 mmol) of 4-pyridineethanesulfonyl chloride is added and the mixture stirred for 17 hrs at room temperature and cooled with an ice bath. A 14 ml (100 mmol) portion of triethylamine is added and stirring continued for 3.5 hrs at room temperature. The dichloromethane is evaporated and water is added to the residue. The pH is adjusted to 9.5 with 1 N sodium hydroxide and the solution acidified with hydrochloric acid. The granular solid is filtered, washed with water, methanol and ether, and dried to give 18.3 g of crude product. The solid is heated at reflux with stirring for 2 hrs in 400 ml of methanol, filtered, washed with methanol and ether, and dried to give 14.5 g of yellow solid. The solid is heated with 150 ml of N,N-dimethylacetamide on a steam bath, cooled in ice, and filtered. The filter cake is washed with methanol and ether and dried to give 7.5 g of product which is heated at reflux with 200 ml of methanol, filtered, washed with methanol and ether and dried to give 6.8 g of 6-[4-[2-(4-pyridinyl)ethylsulfonylamino]phenyl]-1,2-dihydro-2-oxonicotinic acid; mp > 260.

A solution of 5.0 g (12.5 mmol) of the above acid, 3.03 g (18.7 mmol) of carbonyldiimidazole, and 50.0 ml of dry N,N-dimethylacetamide is stirred at 58° for one hour. After standing at room temperature, the reaction suspension is cooled in ice bath to 0°–5° and the product is filtered off, washed with 1.0 ml of N,N-dimethylacetamide three times and then with excess anhydrous ethyl ether and petroleum ether. The dried 6-[4-[2-(4-pyridinyl)ethylsulfonylamino]phenyl]-1,2-dihydro-2-oxonicotinic acid imidazolide weighs 2.85 g.

A suspension of 4.19 g (9.3 mmol) ampicillin triethylamine salt and 40 ml of N,N-dimethylacetamide is stirred at 0°–5° and 2.6 ml (20 mmol) chlorotrimethylsilane is added followed by 1.55 ml (11.1 mmol) of triethylamine. The ice bath is removed and the mixture is stirred at room temperature for 20 min. The reaction mixture is cooled to 0°–5° and 2.8 g (6.2 mmol) of the above imidazolide is added. The ice bath is removed and the reaction is stored at room temperature for four hrs. and allowed to stand at 0° overnight. Insoluble material is filtered off and the filtrate is poured into 800 ml of ice water. The pH is adjusted to 3.5 with 1 N hydrochloric acid and the precipitated solid is filtered, washed with water, acetonitrile, and ether. The solid is dried in a vacuum desiccator over phosphorus pentoxide and then dissolved in 10 ml of dry N,N-dimethylacetamide and 1.5 ml (4.5 mmol) of 50% sodium 2-ethylhexanoate in n-butanol. Five hundred fifty ml of ethyl acetate is added and the product is filtered, washed with ethyl acetate, ether, and dried in a vacuum desiccator over phosphorus pentoxide overnight to give 3.02 g of the title penicillin as the sodium salt; $[\alpha]_D^{23} + 143°$ (cl, 75% DMF/pyridine).

$E_1^1 332 \, \lambda 358$ nm pH 7

EXAMPLE 9

N-[6-[4-(3-pyridinylsulfonylamino)phenyl]-1,2-dihydro-2-oxonicotinoyl]ampicillin A mixture of 34.0 g (0.21 mol) of 3-pyridinesulfonic acid and 47 g (0.24 mol) of phosphorus pentachloride is heated on the steam bath for 2 hrs and the phosphorus oxychloride is removed at reduced pressure to give an oil which crystallize upon addition of chloroform. The solid is filtered, washed with chloroform, and dried under high vacuum to give 38.2 g of 3-pyridinesulfonyl chloride hydrochloride.

A suspension of 11.5 g (50 mmol) of 6-(4-aminophenyl)-1,2-dihydro-2-oxonicotinic acid, 21 ml (150 mmol) of triethylamine, and 500 ml of dichloromethane is stirred at 0°–5° and 20.2 ml (158 mmol) of chlorotrimethylsilane is added. The ice bath is removed and the mixture is stirred at room temperature for 1 hr. The solution is cooled with an ice bath and 11.8 g (55 mmol) of 3-pyridinesulfonyl chloride hydrochloride is added followed by 7 ml (50 mmol) of triethylamine 15 min later. The reaction is stirred at room temperature for 70 hrs, cooled with an ice bath and 3.5 ml (25 mmol) of triethylamine is added. The reaction is stirred at room temperature for 4.5 hrs, cooled with an ice bath, and 11.8 g (55 mmol) of 3-pyridinesulfonyl chloride hydrochloride is added. The mixture is stirred at room temperature for 16 hrs and the dichloromethane is evaporated. Water is added to the residue and the precipitated solid is filtered, washed with water, ether, methanol, and ether, and dried to give 18.8 g of product. This material is combined with 3.2 g from another run and is heated with stirring at reflux for 1.5 hr with 450 ml of methanol. The solid is filtered, washed with methanol and ether and dried to give 19.8 g of 6-[4-(3-pyridinylsulfonylamino)phenyl]-1,2-dihydro-2-oxonicotinic acid; mp>260°.

A solution of 5.57 g (15.0 mmol) of the above acid and 3.65 g (22.5 mmol) of carbonyldiimidazole and 40 ml of N,N-dimethylacetamide is heated at 57° C. for 10 min and then allowed to cool slowly to room temperature. Fifty ml of dry acetonitrile and 700 ml of ethyl ether are added to the reaction solution and the resulting suspension is allowed to stand at 0° C. for one day. The solid is filtered off, washed with ether and dried to give 6.18 g of 6-[4-(3-pyridinylsulfonylamino)phenyl]-1,3-dihydro-2-oxonicotinic acid imidazolide.

A suspension of 7.97 g (17.7 mmol) ampicillin triethylamine salt and 50 ml of N,N-dimethylacetamide is stirred at 0°–5° and 4.98 ml (38 mmol) of chlorotrimethylsilane is added followed by 2.97 ml (21.2 mmol) of triethylamine. The ice bath is removed and the mixture is stirred near room temperature for 20 min. The reaction mixture is cooled to 0°–5° and 5.96 g (14 mmol) of the above imidazolide is added. Th reaction mixture is stirred at room temperature for two hours and then stored at 0° C. for 16 hours. Insoluble material is filtered off and the filtrate is poured into 400 ml of ice water. A slight haze at this point is removed by filtration using Supercel Hyflo ® filter aid. The aqueous filtrate is acidified to pH 2.2 with 1 N hydrochloric acid and then extracted with 200 ml of ethyl acetate three times. The cold combined ethyl acetate extracts are dried over magnesium sulfate, filtered, and the filtrate treated with 4.64 ml of 50% sodium 2-ethylhexanoate in n-butanol. The yellow precipitate is filtered off, washed with ether and dried over phosphorus pentoxide in a vacuum desiccator to give 5.4 of the title penicillin as the sodium salt; $[\alpha]_D^{23} + 159°$ (cl, 75% DMF/pyridine).

$E_1^1 375 \, \lambda \, 374$ nm pH 7

EXAMPLE 10

N-[6-[3-(3-pyridinylsulfonylamino)phenyl]-1,2-dihydro-2-oxonicotinoyl]ampicillin A suspension of 11.5 g (50 mmol) of 6-(3-aminophenyl)-1,2-dihydro-2-oxonicotinic acid and 300 ml of water is stirred at room temperature and 21 g (0.15 mol) of potassium carbonate is added. The solution is cooled to 25° and 13.0 g (61 mmol) of 3-pyridinesulfonyl chloride hydrochloride is slowly added. The solution is clarified by filtration and the pH of the filtrate adjusted to 5.3 with hydrochloric acid. The precipitated solid is filtered, washed with water and dissolved in 300 ml of water containing 10 g (72 mmol) of potassium carbonate. The solution is stirred at room temperature and 10 g (47 mmol) of 3-pyridinesulfonyl chloride hydrochloride is gradually added along with portions of potassium carbonate to maintain a pH of 8. Altogether 10 g (72 mmol) of potassium carbonate is added. The reaction is stirred for 30 min at room temperature and filtered. The pH of the filtrate is adjusted to 6 with hydrochloric acid and the solids filtered and washed with water. A second crop is obtained by lowering the pH of the filtrate to 4.0 and the solid is filtered. The two crops are combined with 200 ml of 1 N sodium hydroxide and heated on the steam bath for 1 hour and filtered. The filtrate is acidified to pH 5.7 with 1 N hydrochloric acid and the solid is filtered, washed with water, methanol, and ether and dried under high vacuum to give 15.2 g of 6-[3-(3-pyridinylsulfonylamino)phenyl]-1,2-dihydro-2-oxonicotinic acid; mp 305° dec.

A mixture of 7.5 g (20 mmol) of the above pyridone acid and 25 ml of thionyl chloride is stirred overnight at room temperature. The solid is filtered, washed with ether and dried under high vacuum over phosphorus pentoxide to give 8.62 g of 6-[3-(3-pyridinylsulfonylamino)phenyl]-1,2-dihydro-2-oxonicotinic acid chloride hydrochloride.

A suspension of 5.65 g (12.5 mmol) of ampicillin triethylamine salt and 50 ml of tetrahydrofuran is stirred at 0°–5°. and 3.55 ml (22 mmol) of chlorotrimethylsilane is added followed by 5.7 ml (40.7 mmol) of triethylamine. The reaction mixture is stirred for 30 minutes and 5.9 g (13.9 mmol) of the above acid chloride is added followed by 20 ml of tetrahydrofuran 20 minutes later. The reaction is stirred for 1 hour and refrigerated overnight. The reaction is diluted to 1 liter with cold water and the precipitate is extracted into ethyl acetate. The combined extracts are clarified by filtration and 5 ml of sodium 2-ethylhexanoate (50% in n-butanol) is added followed by an equal volume of ether. The mixture is refrigerated overnight and the solvents decanted from the precipitate. A 200 ml portion of ether is added and the solid is filtered and dried to give 3.57 g of crude product. Three grams of the product is dissolved in 30 ml of methanol at 0°–5° and 5 fractions are collected by addition of small amounts of isopropanel followed by filtration and addition of isopropanol to the filtrate. The last fraction is obtained by addition of 20 ml of isopropanol and 30 ml of ether. The three best fractions, totaling 2.36 g are combined and dissolved in 23.6 ml of methanol at 0°–5° and 17 ml of isopropanol is added. The solid is filtered and discarded and isopropanol and ether are added to the filtrate. The precipitate is filtered, washed with ether, and dried under high vacuum over prosphorus pentoxide to give 1.24 g of the title penicillin; $[\alpha]_D^{25} + 129°$ (cl, 75% DMF/pyridine).

$E_1^1 283 \lambda 347$ nm pH 7

We claim:

1. A compound of the formula

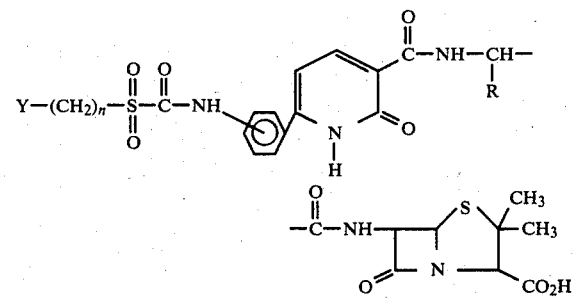

and pharmaceutically acceptable salts thereof; wherein Y is hydrogen, $CF_3$, hydroxy, pyridyl,

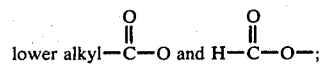

n is 0, 1, 2 or 3 and R is phenyl, 4-hydroxyphenyl, 2-thienyl or cyclohexa-1,4-dien-1-yl with the proviso that when Y is

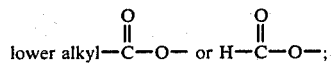

n is 1, 2 or 3.

2. The compound of claim 1 having the name N-[6-[3-(Methylsulfonylamino)phenyl]-1,2-dihydro-2-oxonicotinoyl]ampicillin and pharmaceutically acceptable salts thereof.

3. The compound of claim 1 having the name N-[6-[4-(methylsulfonylamino)phenyl]-1,2-dihydro-2-oxonicotinoyl]ampicillin and pharmaceutically acceptable salts thereof.

4. The compound of claim 1 having the name N-[6-[4-(methylsulfonylamino)phenyl]-1,2-dihydro-2-oxonicotinoyl]amoxicillin and pharmaceutically acceptable salts thereof.

5. The compound of claim 1 having the name N-[6-[4-(Propylsulfonylamino)phenyl]-1,2-dihydro-2-oxonicotinoyl]ampicillin and pharmaceutically acceptable salts thereof.

6. The compound of claim 1 having the name N-[6-[4-(Trifluoromethylsulfonylamino)phenyl]-1,2-dihydro-2-oxonicotinoyl]ampicillin and phrmaceutically acceptable salts thereof.

7. The compound of claim 1 having the name N[6-[4-(Trifluoromethylsulfonylamino)phenyl]-1,2-dihydro-2-oxonicotinoyl]amoxicillin and pharmaceutically acceptable salts thereof.

8. The compound of claim 1 having the name N-[6-[4-[3-(acetyloxy)propylsulfonylamino]phenyl]-1,2-dihydro-2-oxonicotinoyl]ampicillin and pharmaceutically acceptable salts thereof.

9. The compound of claim 1 having the name N-[6-4-[2-(4-pyridinyl)ethylsulfonylamino]phenyl]-1,2-dihydro-2-oxonicotinoyl]ampicillin and pharmaceutically acceptable salts thereof.

10. The compound of claim 1 having the name N-[6-[4-(3-pyridinylsulfonylamino)phenyl]-1,2-dihydro-2-oxonicotinoyl]ampicillin and pharmaceutically acceptable salts thereof.

11. The compound of claim 1 having the name N-[6-[3-(3-pyridinylsulfonylamino)phenyl]-1,2-dihydro-2-oxonicotinoyl]ampicillin and pharmaceutically acceptable salts thereof.

12. An antibacterial pharmaceutical composition comprising from 50 mg to 1000 mg of a compound of claim 1 and a pharmaceutical carrier.

13. A method for treating bacterial infections which comprises administering 5 mg to 100 mg per kg to an infected mammal of the pharmaceutical composition of claim 12.

14. A compound of the formula

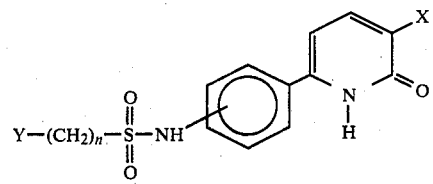

where Y and n are as defined in claim 1 and X is cyano, carboxy, or a carboxylate salt.

* * * * *